(12) United States Patent
Hill et al.

(10) Patent No.: US 8,741,228 B2
(45) Date of Patent: Jun. 3, 2014

(54) HYDROGEN PEROXIDE VAPORIZER WITH HEATED DIFFUSER

(75) Inventors: Aaron Leif Hill, Madison, OH (US); Ryan Anthony Bruskevith, Mentor, OH (US); Jeffrey Allan Goughnour, Erie, PA (US)

(73) Assignee: American Sterilizer Company, Mentor, OH (US)

( * ) Notice: Subject to any disclaimer, the term of this patent is extended or adjusted under 35 U.S.C. 154(b) by 334 days.

(21) Appl. No.: 13/242,427

(22) Filed: Sep. 23, 2011

(65) Prior Publication Data

US 2013/0078143 A1   Mar. 28, 2013

(51) Int. Cl.
*A61L 9/00* (2006.01)
*B01J 7/00* (2006.01)
*A61L 2/00* (2006.01)
*A61L 2/18* (2006.01)
*A62B 7/08* (2006.01)

(52) U.S. Cl.
USPC ............. 422/306; 422/28; 422/292; 422/120; 422/123; 422/124; 422/125

(58) Field of Classification Search
CPC ... A61L 2202/15; A61L 9/03; A61L 2202/16; A61L 2202/25
USPC ............ 422/120, 123, 124, 125, 292, 306, 28
See application file for complete search history.

(56) References Cited

U.S. PATENT DOCUMENTS

| | | | |
|---|---|---|---|
| 2,690,380 A | 9/1954 | Taylor | 23/204 |
| 4,537,749 A | 8/1985 | Hick | 422/304 |
| 4,742,667 A | 5/1988 | Müller et al. | 53/167 |
| 5,007,232 A | 4/1991 | Caudill | 53/426 |
| 5,152,968 A | 10/1992 | Foti et al. | 422/304 |
| 5,835,677 A | 11/1998 | Li et al. | 392/401 |
| 5,906,794 A | 5/1999 | Childers | 422/28 |
| 6,406,666 B1 | 6/2002 | Cicha et al. | 422/28 |
| 6,746,652 B2 | 6/2004 | Khorzad et al. | 422/305 |
| 7,156,957 B1 | 1/2007 | Parrish et al. | 204/157.3 |
| 7,186,374 B2 | 3/2007 | Zelina et al. | 422/28 |
| 7,252,800 B2 | 8/2007 | Jacobs et al. | 422/33 |
| 2005/0084415 A1 | 4/2005 | McVey et al. | 422/28 |
| 2005/0095168 A1 | 5/2005 | Centanni et al. | 422/3 |
| 2006/0270887 A1 | 11/2006 | Watkins | 588/300 |
| 2006/0289490 A1* | 12/2006 | Mielnik | 219/628 |
| 2007/0003431 A1 | 1/2007 | Kendall et al. | 422/28 |
| 2007/0053813 A1* | 3/2007 | Martin | 422/295 |
| 2007/0253859 A1 | 11/2007 | Hill | 422/3 |
| 2008/0041230 A1 | 2/2008 | Takahashi et al. | 96/236 |
| 2008/0233001 A1* | 9/2008 | Ricciardi et al. | 422/20 |
| 2008/0247922 A1 | 10/2008 | Adams et al. | 422/292 |
| 2010/0034707 A1* | 2/2010 | Mielnik et al. | 422/122 |
| 2011/0114744 A1* | 5/2011 | Ricciardi et al. | 239/4 |

* cited by examiner

*Primary Examiner* — Regina M Yoo
(74) *Attorney, Agent, or Firm* — Kusner & Jaffe; Michael A. Centanni

(57) ABSTRACT

The present invention provides an apparatus for decontaminating a region. The apparatus includes a housing that defines a chamber therein. The housing has an inlet and an outlet that communicate with the chamber. A blower circulates a carrier gas from the region, through the inlet of the housing, through the chamber and out through the outlet of the housing. An atomizer introduces an atomized mist of a fluid into the carrier gas circulated through the chamber. A diffuser is disposed relative to the outlet of the chamber for redirecting said carrier gas exiting said outlet of said chamber into a predetermined direction. The diffuser includes a heating element.

19 Claims, 4 Drawing Sheets

HYDROGEN PEROXIDE VAPORIZER WITH HEATED DIFFUSER

FIELD OF THE INVENTION

The present invention relates to decontaminating a region and articles disposed therein, and more particularly, to an apparatus for decontaminating a region and articles disposed therein using a vaporous chemical agent.

BACKGROUND OF THE INVENTION

A region, defined by an enclosure, (e.g., hotel rooms, offices, laboratories, buildings, cruise ships, airport terminals, and the like) may be decontaminated by exposing the region (and any articles therein) to a vaporous chemical agent, such as vaporized hydrogen peroxide. Vaporized hydrogen peroxide may be generated by vaporizing a metered quantity of an aqueous solution of hydrogen peroxide (e.g., about 30% to 59% hydrogen peroxide, by weight). The vaporized hydrogen peroxide is carried into the region by a carrier gas (e.g., air). As used herein the term "decontamination" refers to the inactivation of bio-contamination, and includes, but is not limited to, sterilization and disinfection.

Conventional systems for decontaminating a region vaporize an aqueous solution of hydrogen peroxide using heat. In some applications, the vaporized hydrogen peroxide is produced by dripping an aqueous solution of hydrogen peroxide onto a heated surface. The hydrogen peroxide vaporizes upon contact with the heated surface. In other applications, the aqueous solution of hydrogen peroxide is injected into a stream of heated air. The heated air causes the aqueous solution of hydrogen peroxide to vaporize upon injection therein. Conventional systems, such as those described above, require relatively large amounts of power (e.g., 10,000 watts) to generate the vaporized hydrogen peroxide.

The present invention overcomes the aforementioned problem and provides a method and apparatus that effectively and efficiently vaporizes hydrogen peroxide at an ambient air temperature in a region.

SUMMARY OF THE INVENTION

In accordance with a preferred embodiment of the present invention, there is provided an apparatus for decontaminating a region. The apparatus includes a housing that defines a chamber therein. The housing has an inlet and an outlet that communicate with the chamber. A blower circulates a carrier gas from the region, through the inlet of the housing, through the chamber, through the outlet of the housing and back to the region. An atomizer introduces an atomized mist of a fluid into the carrier gas circulated through the chamber. A diffuser is disposed relative to the outlet of the chamber for redirecting said carrier gas exiting said outlet of said chamber into a predetermined direction. The diffuser includes a heating element.

In accordance with yet another embodiment of the present invention, there is provided a method for decontaminating a region. The method includes the steps of: a) circulating a carrier gas from the region through a chamber defined by a housing; b) introducing an atomized mist of a chemical agent into the chamber to form a vaporous chemical agent, wherein the vaporous chemical agent is entrained into the carrier gas to form a mixture; c) conveying the mixture out of the chamber along a pathway back to the region, wherein the pathway is partially defined by a diffuser; and d) heating the diffuser as the mixture is conveyed through the pathway.

An advantage of the present invention is the provision of an apparatus for decontaminating a region defined by an enclosure using a vaporous chemical agent.

Yet another advantage of the present invention is the provision of an apparatus as described above that requires less power as compared to conventional apparatuses.

Still another advantage of the present invention is the provision of an apparatus as described above that vaporizes the chemical agent at the temperature of the ambient air in the region.

Still another advantage of the present invention is the provision of an apparatus as described above that heats a diffuser to prevent the chemical vapor from condensing thereon.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF A PREFERRED EMBODIMENT

Figure 1:
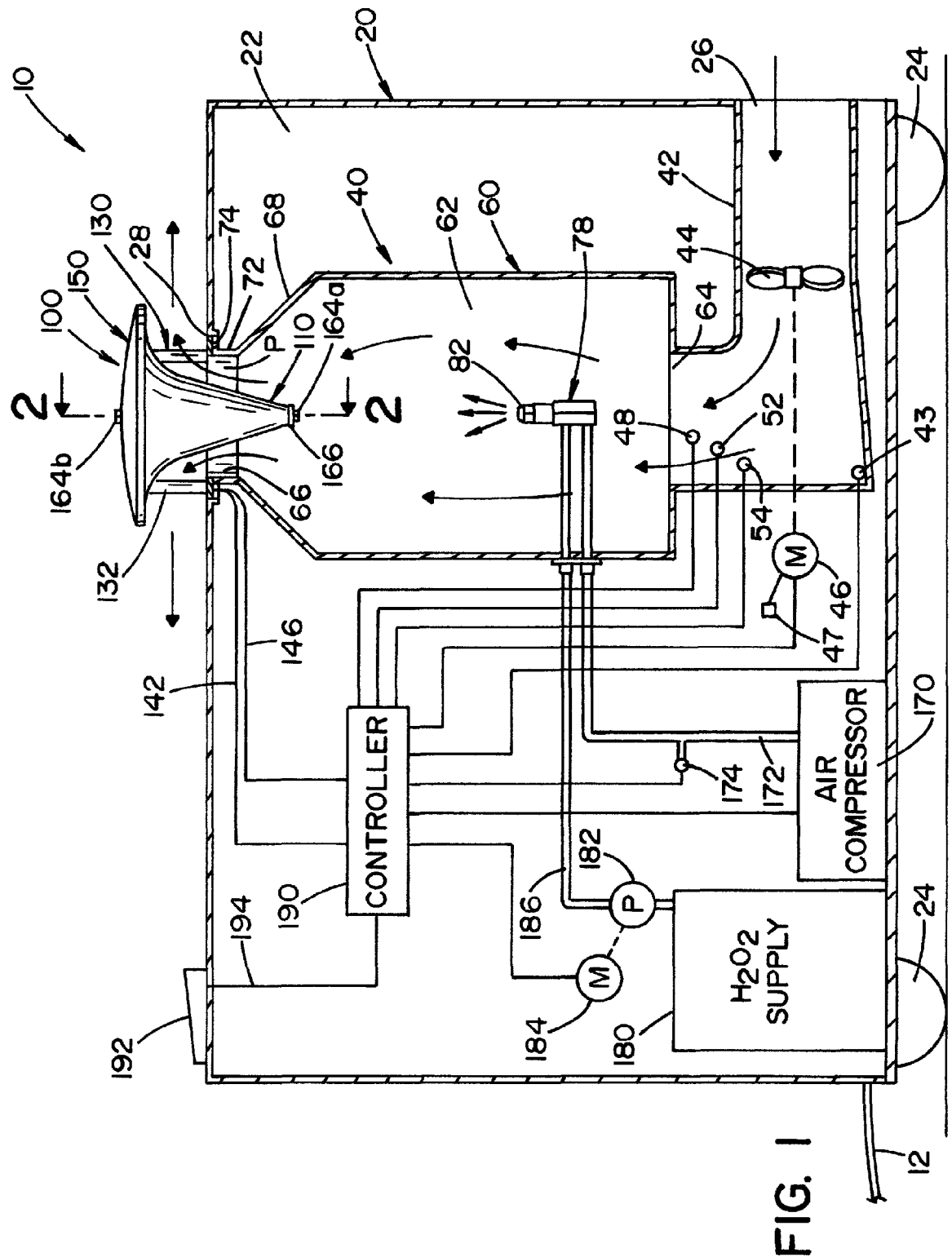
FIG. 1 is a schematic view of an apparatus for decontaminating a region defined by an enclosure.

Referring now to the drawings wherein the showings are for the purpose of illustrating an embodiment of the invention only, and not for the purpose of limiting same, FIG. 1 shows a schematic view of decontamination unit 10 for decontaminating a region defined by an enclosure. The present invention will be described hereinafter with reference to using vaporized hydrogen peroxide to decontaminate a region. However, it is appreciated that unit 10 may be adapted to decontaminate a region with other types of chemical agents.

Unit 10 is generally comprised of an outer housing member 20, an inner flow assembly 40, a diffuser 100, an air compressor 170, a reservoir 180 and a controller 190. A cable 12 is provided for connecting the components of unit 10 that require power to a power source (not shown). In one embodiment, the power source is a conventional North American electrical outlet, i.e., 120 VAC, 20 amp electrical power supply. Inner flow assembly 40, diffuser 100, air compressor 170, reservoir 180 and controller 190 are disposed in an inner cavity 22 defined by outer housing member 20.

Wheels 24 are attached to outer housing member 20 to allow for convenient movement of unit 10. It is contemplated that wheels 24 may be connected to an on-board motorized system (not shown) that is programmable or controlled remotely by a user. Outer housing member 20 includes a first opening 26 and a second opening 28. First opening 26 extends through a side wall of outer housing member 20 and second opening 28 extends through a top wall of outer housing member 20. It is contemplated that first opening 26 and second opening 28 may extend through other walls of outer housing member 20.

Inner flow assembly 40 is generally comprised of a conduit 42, a blower 44, and an inner housing 60.

Conduit 42 includes an inlet end that communicates with first opening 26 of outer housing member 20 and an outlet end that communicates with inner housing 60, described in detail below. A bottom wall of conduit 42 is sloped downwardly toward a corner of conduit 42 to define a low region or sump of conduit 42. A proximity sensor 43 is disposed in the sump of conduit 42. Sensor 43 provides a signal indicative of the presence or absence of aqueous hydrogen peroxide in the sump of conduit 42.

Blower 44 is disposed within conduit 42 for conveying ambient air from the inlet end of conduit 42 to the outlet end of conduit 42. In one embodiment, blower 44 circulates air through conduit 42 at a rate of about 600 cubic feet per minute (CFM). Blower 44 is driven by a motor 46. A current sensor 47 is attached to power leads that extend from motor 46 to provide a signal indicative of the amount of current passing through motor 46.

A temperature sensor 48, a humidity sensor 52 and a vaporized hydrogen peroxide (VHP) sensor 54 are disposed in conduit 42. Temperature sensor 48 provides a signal indicative of the temperature of the air in the region. Humidity sensor 52 provides a signal indicative of the water vapor concentration (e.g., relative humidity (RH)) within the region. Absolute humidity may be determined from the temperature and RH sensed respectively by temperature sensor 48 and humidity sensor 52, or alternatively humidity sensor 52 can take the form of a sensor that directly measures absolute humidity. VHP sensor 54 provides a signal indicative of the concentration of vaporized hydrogen peroxide in the air in the region. VHP sensor 54 is preferably a near infrared (IR) sensor or an electrochemical sensor. It is contemplated that one or more of temperature sensor 48, humidity sensor 52 and VHP sensor 54 may be disposed external to outer housing member 20.

Figure 2:
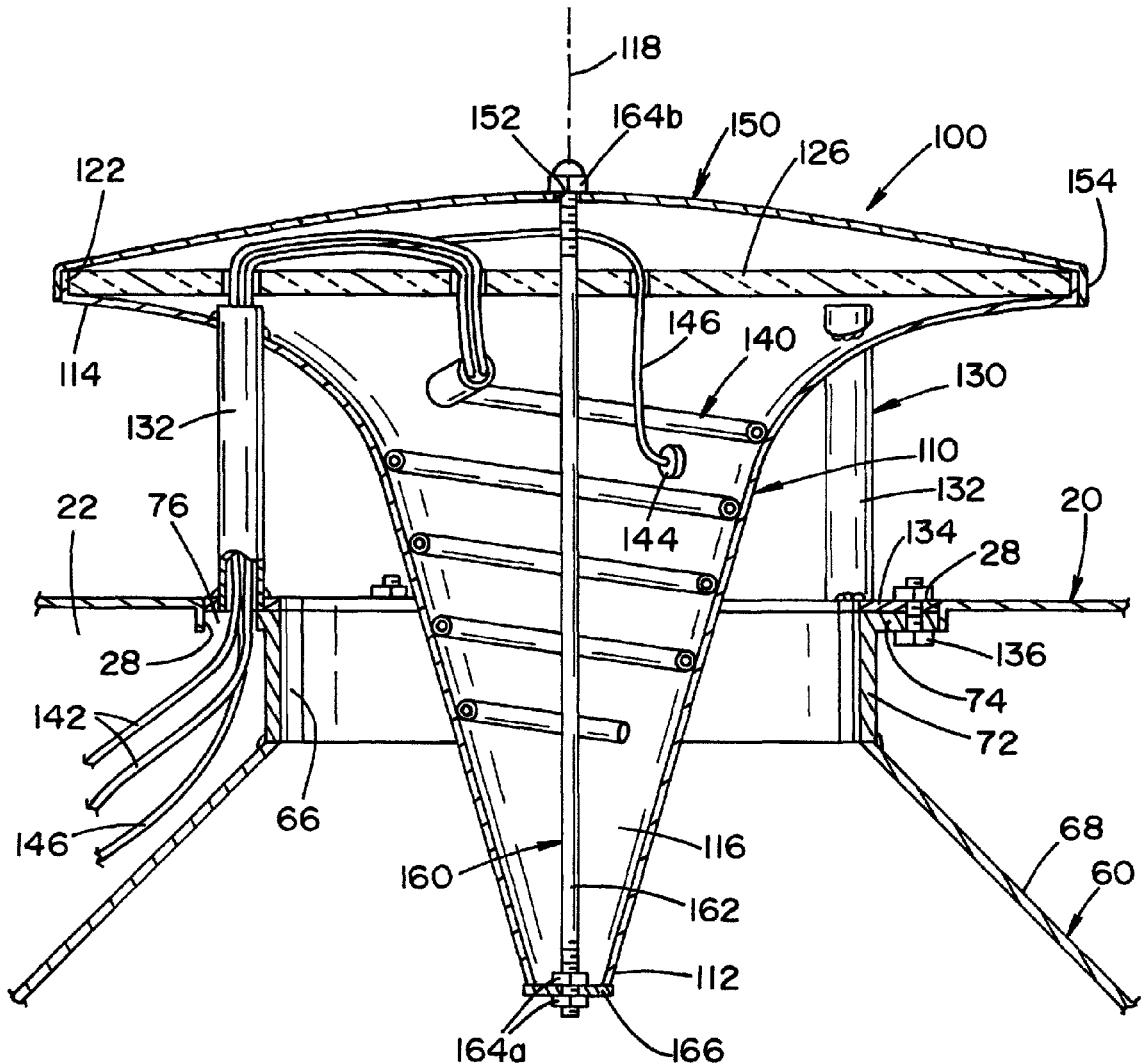
FIG. 2 is a cross-sectional view of the apparatus taken along lines 2-2 in FIG. 1.

Inner housing 60 defines a vaporization chamber 62 therein. An inlet 64 and an outlet 66 are formed in inner housing 60 to communicate with chamber 62. Inlet 64 of inner housing 60 communicates with the outlet end of conduit 42. Outlet 66 of inner housing 60 communicates with second opening 28 of outer housing member 20. As best seen in FIG. 2, an upper section of inner housing 60 includes a tapered portion 68 and a collar portion 72. Collar portion 72 defines outlet 66 of inner housing 60. An outwardly extending annular flange 74 extends outwardly from an end of collar portion 72. Flange 74 includes a notch 76 (best seen in FIG. 3) and a plurality of holes that will be described in detail below.

Figure 3:
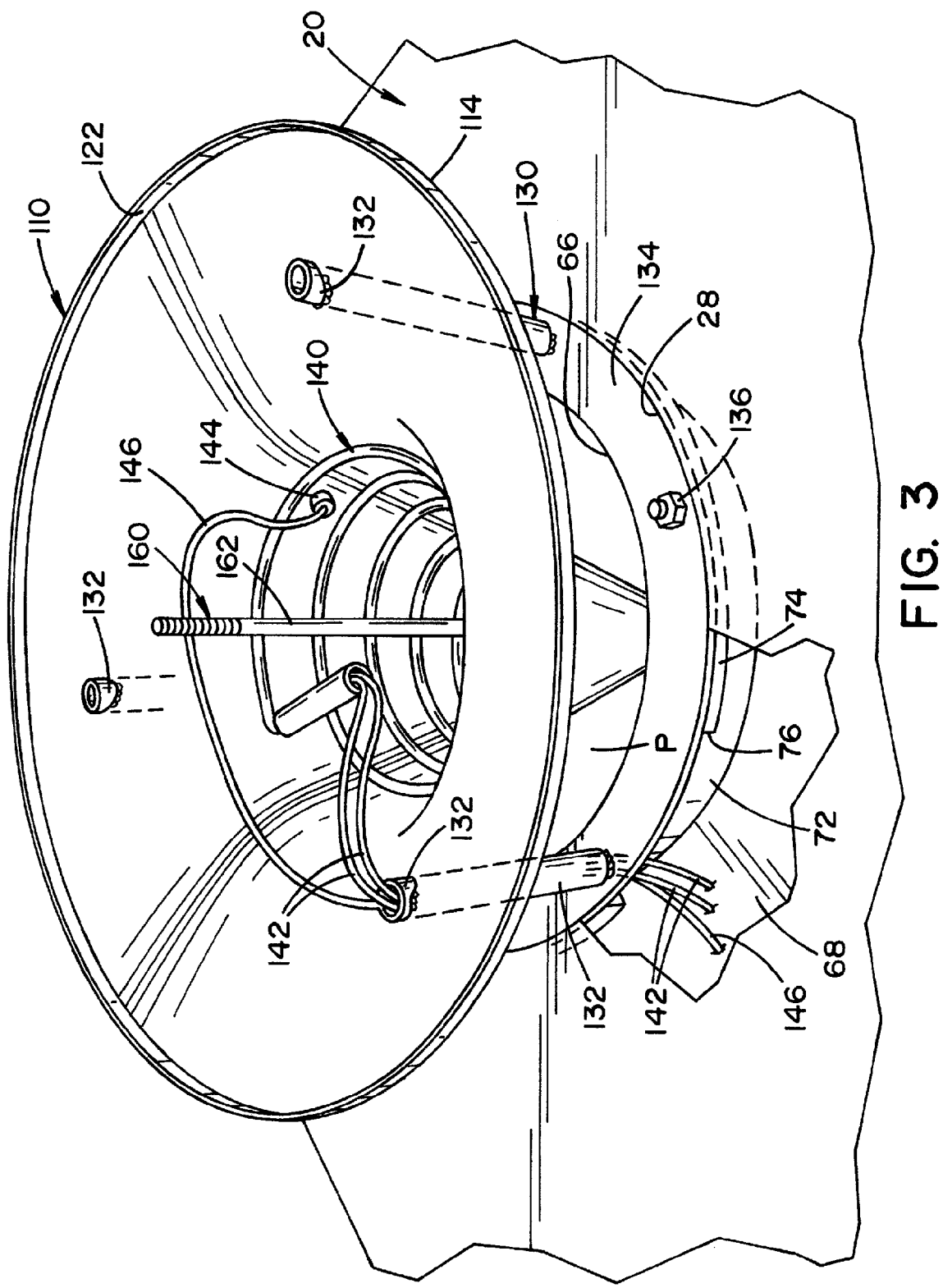
FIG. 3 is a side perspective view of the diffuser shown in FIG. 2, wherein a lid of the diffuser is removed.

Referring now to FIGS. 2-3, diffuser 100 will now be described in detail. Diffuser 100 is dimensioned to mount to flange 74 of inner housing 60. Diffuser 100 is generally comprised of a main body 110, a disc-shaped insulator 126, a mounting support assembly 130, a heating element 140, a lid 150 and an attachment assembly 160.

Main body 110 is funnel-shaped with a first end 112 and a second end 114. Main body 110 defines a funnel-shaped interior space 116 that extends from first end 112 to second end 114. A main axis 118 of main body 110 extends between first end 112 and second end 114. In the embodiment shown, the diameter of main body 110 increases continuously from a first diameter at first end 112 to a second diameter at second end 114. Second end 114 of main body 110 is formed to define a curved flange portion of main body 110. An annular flange 122 extends from a periphery of second end 114 of main body 110.

Mounting support assembly 130 includes a plurality of spacers 132 and a mounting collar 134. Mounting support assembly 130 mounts diffuser 100 to inner housing 60. In the illustrated embodiment, spacers 132 are tubular elements. A first end of each spacer 132 is attached to main body 110. In particular, the first end of each spacer 132 extends through the wall of main body 110. A second end of each spacer 132 is attached to mounting collar 134.

Collar 134 is a generally flat, ring-shaped element. Collar 134 includes a plurality of holes therein. Each hole is dimensioned to receive a fastener 136.

Heating element 140 heats main body 110 of diffuser 100. In the illustrated embodiment, heating element 140 is a spiral-shaped, resistive heating element that is disposed within interior space 116 of main body 110. It is contemplated that heating element 140 may have other shapes, such as, but not limited to, circular, or rectangular. Heating element 140 preferably is in contact with the inner surface of main body 110, as shown in FIG. 2, to facilitate conductive heating of main body 110. Cables 142 extend from heating element 140 to controller 190.

A temperature sensor 144 is disposed in interior space 116 of main body 110 to provide a signal indicative of the temperature of main body 110. Temperature sensor 144 preferably is in contact with the inner surface of main body 110. A cable 146 extends from temperature sensor 144 to controller 190.

Disc-shaped insulator 126 is disposed in second end 114 of main body 110 to retain heat within interior space 116 of main body 110. Insulator 126 includes a plurality of holes extending therethrough. Insulator 126 has an outer diameter slightly smaller than a diameter of annular flange 122 of main body 110.

Lid 150 covers second end 114 of main body 110 to enclose interior space 116. Lid 150 is generally disc-shaped with a hole 152 extending through a central portion thereof. An annular mating flange 154 extends from a periphery of the lower surface of lid 150. In the embodiment shown, lid 150 is generally convex in shape.

Attachment assembly 160 secures lid 150 to main body 110. Attachment assembly 160 includes a rod 162, fasteners 164a, 164b and a washer 166. A first end and a second end of rod 162 include threads formed thereon. Fasteners 164a, 164b thread onto rod 162. Washer 166 is dimensioned to be disposed on the first end of rod 162.

As shown in FIG. 2, annular flange 154 of lid 150 mates with annular flange 122 of main body 110 to enclose second end 114 of main body 110. The first end of rod 162 extends through the opening in first end 112 of main body 110 and the second end of rod 162 extends through a hole in insulator 126 and through hole 152 in lid 150. Washer 166 and two fasteners 164a are placed on the first end of rod 162. Washer 166 has an outer diameter slightly larger than the opening in first end 112 of main body 110. Fastener 164b is threaded onto the second end of rod 162. As fastener 164b is tightened, lid 150 and main body 110 are clamped between washer 166 on the first end of rod 162 and fastener 164b on the second end of rod 162. In this respect, lid 150 and washer 166 are attached to and secured to main body 110 to enclose interior space 116 defined by main body 110.

As noted above, diffuser 100 is mounted to flange 74 of inner housing 60 using fasteners 136. In particular, diffuser 100 is positioned on flange 74 such that notch 76 in flange 74 of inner housing 60 aligns with one spacer 132 of diffuser 100 and the plurality of holes in collar 134 of diffuser 100 are in registry with the plurality of holes in flange 74 of inner housing 60, as best seen in FIG. 3. Fasteners 136 secure diffuser 100 to inner housing 60.

According to the present invention, main body 110 of diffuser 100 and collar portion 72 of inner housing 60 define a pathway "P" therebetween. Pathway "P" is designed to allow air flow therethrough at a predetermined flow rate and to cause air flowing therethrough to be exhausted into the region in a predetermined direction, as will be described in detail below.

Referring now to FIG. 1, atomizer 78 is disposed within chamber 62. Atomizer 78 includes a nozzle 82 that is oriented toward diffuser 100. In the embodiment shown, atomizer 78 produces droplets that are approximately 2 microns in diameter.

Air compressor 170 is provided to supply a pressurized gas to atomizer 78. A line 172 connects air compressor 170 to atomizer 78. A pressure sensor 174 is disposed in line 172. Pressure sensor 174 provides a signal indicative of the pressure of the gas in line 172.

Reservoir 180 is provided for holding a predetermined amount of an aqueous solution of hydrogen peroxide. A line 186 connects reservoir 180 to atomizer 78. A pump 182 is disposed in line 186 to convey metered amounts of the aqueous solution of hydrogen peroxide from reservoir 180 to atomizer 78. In the embodiment shown, pump 182 includes an encoder (not shown) that allows monitoring of the amount of the aqueous solution of hydrogen peroxide that is metered to atomizer 78. Pump 182 is driven by a motor 184. Motor 184 may have variable speeds to provide variable amounts of the aqueous solution of hydrogen peroxide from reservoir 180 to atomizer 78.

Controller 190 may include a microprocessor or microcontroller, memory device(s) and a wireless communications interface. An input/output means 192 (e.g., an LED or LCD display) is connected by a cable 194 to controller 190. Cables 142 are connected at one end to controller 190 and at another end to heating element 140 to allow controller 190 to control the operation of heating element 140. Cable 146 is connected at one end to temperature sensor 144 and at another end to controller 190. In particular, cables 142, 146 extend from controller 190 through notch 76 in flange 74 through one spacer 132 to heating element 140 and to temperature sensor 144, respectively. Controller 190 also communicates with air compressor 170, motors 46, 184, proximity sensor 43, current sensor 47, temperature sensors 48, 144, humidity sensor 52, VHP sensor 54 and pressure sensor 174. Controller 190 is programmed to control the operation of unit 10, as described below.

The operation of unit 10 will now be described in connection with the decontamination of a region. Controller 190 is programmed to control the operation of motors 46, 184, heating element 140 and air compressor 170 during a decontamination cycle. Controller 190 initiates the decontamination cycle by energizing motor 46. Motor 46 activates blower 44 thereby drawing ambient air from the region into unit 10. The ambient air is circulated through conduit 42, through vaporization chamber 62 and exits through second opening 28 of outer housing member 20 back into the region. Current sensor 47 provides a signal to controller 190 indicative of the amount of current passing through motor 46. Based on the foregoing signal, controller 190 determines whether motor 46 is operating within predetermined acceptable operating parameters.

Controller 190 then energizes heating element 140 to heat diffuser 100. Insulator 126 is provided to retain heat within interior space 116 of diffuser 100. With respect to the maximum power available to heating element 140 of diffuser 100, in the case where unit 10 receives power from a conventional North American electrical outlet, i.e., 120 VAC, 20 amp electrical power, it is assumed that only 80% of the total amps available is used (i.e., 16 amps). As a result, the total amount of average power available to unit 10 is about 1920 watts. In order to maximize the amount of average power that may be available to heating element 140, the components of unit 10 that may affect the consumption of electrical power are sized to minimize the amount of average electrical power that they require. In particular, vaporization chamber 62 is designed so that the pressure drop through chamber 62 is as low as possible. The lower the pressure drop through chamber 62 the less power required by blower 44 to circulate air through chamber 62 at a predetermined flow rate. According to one embodiment of the present invention, blower 44 requires 160 watts of power, air compressor 170 requires 260 watts of power and controller 190 requires 100 watts of power. In this embodiment of the present invention, 1400 watts of power is available for heating element 140.

When diffuser 100 reaches a predetermined temperature, as measured by temperature sensor 144, controller 190 energizes air compressor 170 to supply pressurized gas to atomizer 78 and energizes motor 184 to cause pump 182 to supply the aqueous solution of hydrogen peroxide to atomizer 78. In particular, controller 190 controls the speed of motor 184 to cause pump 182 to supply the aqueous solution of hydrogen peroxide to atomizer 78 at a predetermined rate. Pressure sensor 174 provides a signal to controller 190 indicative of the pressure in line 172. Based on the foregoing signal from pressure sensor 174, controller 190 determines whether air compressor 170 is operating within predetermined acceptable operating parameters. Atomizer 78 combines the pressurized gas from air compressor 170 and the aqueous solution of hydrogen peroxide from reservoir 180 to form a fine mist of aqueous hydrogen peroxide that is injected into vaporization chamber 62. In the illustrated embodiment, atomizer 78 is centrally located within inner housing 60 in order to hinder the fine mist of aqueous hydrogen peroxide from being sprayed onto the walls of inner housing 60. The atomized mist of hydrogen peroxide vaporizes in the ambient air to form vaporized hydrogen peroxide. The vaporized hydrogen peroxide is entrained into the ambient air circulated through chamber 62. In this respect, the ambient air acts as a carrier gas and mixes with the vaporized hydrogen peroxide to form an air/VHP mixture.

As noted above, conduit 43 includes a lower portion or sump. In the event that a portion of the aqueous hydrogen peroxide does not vaporize in chamber 62, the aqueous hydrogen peroxide will drip downwardly in chamber 62 and collect in the sump of conduit 42. Proximity sensor 43, disposed in the sump of conduit 42, provides a signal to controller 190 if a predetermined amount of aqueous hydrogen peroxide collects in the sump of conduit 42. Controller 190 is programmed such that upon receipt of the foregoing signal from proximity sensor 43, controller 190 de-energizes motor 184 and provides an alarm to the user indicating that excess aqueous hydrogen peroxide has accumulated in conduit 42.

The vaporization of hydrogen peroxide in chamber 62 causes the temperature of the air/VHP mixture in chamber 62 to decrease due to the "evaporative cooling" process (i.e., the cooling of a surrounding air due to the evaporation of a liquid). The cooled air/VHP mixture exiting chamber 62 will cause diffuser 100 to cool to a temperature below the ambient air temperature in the region. If diffuser 100 cools to a temperature below the dew point of hydrogen peroxide, then the hydrogen peroxide in the air/VHP mixture will condense on the surfaces of diffuser 100.

As noted above, diffuser 100 includes heating element 140. Controller 190 energizes heating element 140 to heat diffuser 100. According to the present invention, diffuser 100 is heated to a sufficient temperature to prevent the hydrogen peroxide in the air/VHP mixture from condensing on diffuser 100.

The present invention thus provides a method and apparatus for decontaminating a region wherein the apparatus may be connected to a conventional North American electrical outlet. The present invention is designed to vaporize hydrogen peroxide at the ambient air temperature in the region, thereby eliminating the need to use heat to vaporize hydrogen peroxide. As a result, the present invention requires less power to decontaminate a region as compared to conventional systems. Conventional systems for vaporizing hydrogen peroxide require large amounts of power to heat a surface or a carrier gas, thereby limiting their use in applications where only conventional 120 VAC, 20 amps electrical circuits are available.

As noted above, the air/VHP mixture formed in chamber 62 is conveyed from chamber 62 and through pathway "P." In particular, diffuser 100 is spaced from collar portion 72 to allow the air/VHP mixture to flow through pathway "P" at a predetermined flow rate. Further, the outer surface of diffuser 100 is dimensioned to cause the air/VHP mixture to be exhausted into the region in a predetermined direction. In one embodiment, diffuser 100 causes the air/VHP mixture to be exhausted into the region in a direction generally parallel to a floor of the enclosure that defines the region, as illustrated in FIG. 1. In this embodiment, diffuser 100 changes the direction of the air/VHP mixture by approximately 90 degrees from the direction that the air/VHP mixture is conveyed through chamber 62. Further, according to another embodiment of the present invention, diffuser 100 is dimensioned and positioned relative to collar portion 72 to cause the air/VHP mixture to be exhausted into the region in a radially outward pattern from unit 10.

The present invention thereby provides an apparatus that includes a diffuser that causes an air/VHP mixture to be exhausted into a region in a desired direction. According to the embodiment shown, the air/VHP mixture is exhausted into the region in a 360° pattern in a direction generally parallel to a floor of the enclosure. The desired direction is selected to maximize the distribution of the air/VHP mixture into the region. Moreover, the diffuser of the present invention redirects the air/VHP mixture into a radially outward pattern to improve the distribution of the air/VHP mixture into the region.

Figure 4:
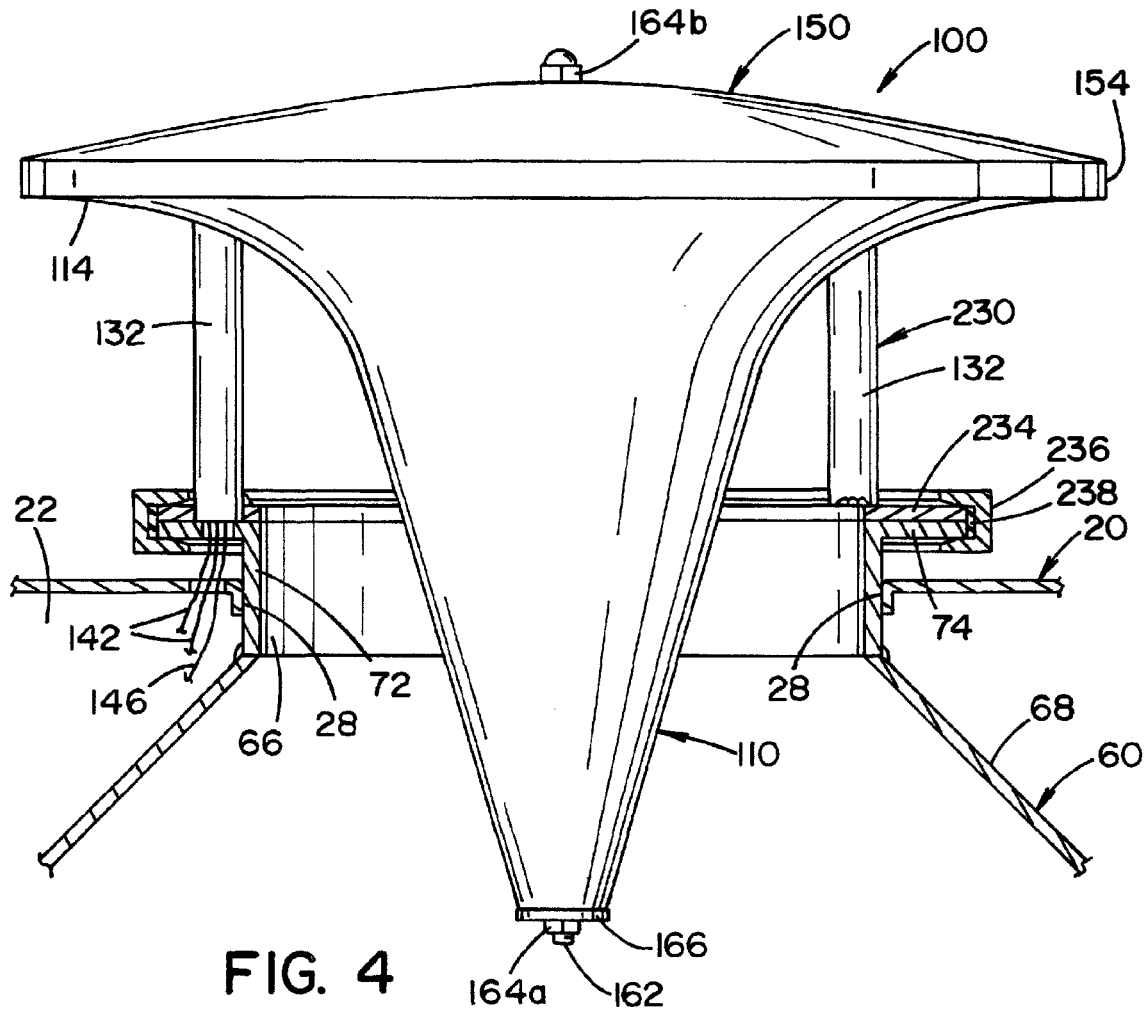
FIG. 4 is a partial cross-sectional view of the apparatus taken along lines 2-2 in FIG. 1 showing another embodiment of the present invention.
Figure 5:
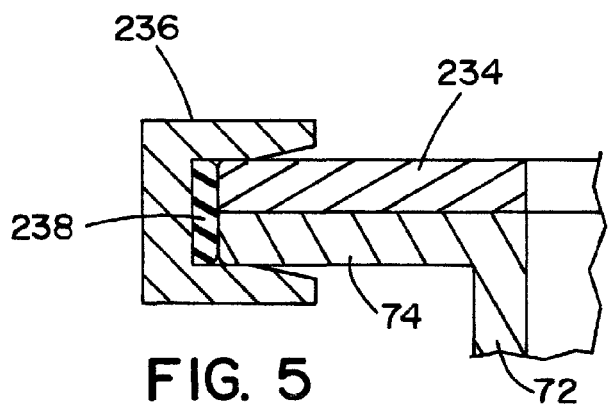
FIG. 5 is an enlarged cross-sectional view of a mounting assembly of the embodiment shown in FIG. 4.

According to another embodiment of the present invention shown in FIGS. 4 and 5, diffuser 100 includes a mounting support assembly 230 that allows for quick and easy attachment/detachment of diffuser 100 to/from vaporization chamber 40. In this embodiment, collar portion 72 of inner housing 60 extends through outlet opening 28 in outer housing member 20 such that flange 74 is disposed outside of outer housing member 20.

Mounting support assembly 230 is attachable to flange 74. Mounting support assembly 230 is generally comprised of a mounting collar 234, a clamp 236, and a gasket 238. Mounting collar 234 is dimensioned to mate with flange 74 on collar portion 72. Gasket 238 is dimensioned to be disposed around an outer peripheral edge of flange 74 and collar 234, as shown in FIG. 5. Clamp 236 is similar to a conventional drum locking ring and includes a ring portion and a locking/unlocking mechanism (not shown). The ring portion of clamp 236 has a C-shaped cross section that is dimensioned to receive mounting collar 234, gasket 238 and flange 74 therein. The ring portion includes a gap formed therein wherein the locking/unlocking mechanism is disposed. The locking/unlocking mechanism of clamp 236 is designed for locking/unlocking clamp 236 around mounting collar 234, gasket 238 and flange 74. In this respect, mounting support assembly 230 is provided for easily and quickly attaching/detaching diffuser 100 to/from flange 74 of inner housing 60.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. An apparatus for decontaminating a region defined by an enclosure, said apparatus including:
    a housing defining a chamber therein, said housing having an inlet and an outlet communicating with said chamber;
    a blower for circulating a carrier gas from said region, through said inlet of said housing, through said chamber, through said outlet of said housing and back to said region;
    an atomizer for introducing an atomized mist of a fluid into said chamber; and
    a diffuser disposed relative to said outlet of said housing for redirecting said carrier gas exiting said outlet of said housing into a predetermined direction, said diffuser including a heating element.

2. The apparatus as defined in claim 1, wherein said apparatus further comprises:
    an air compressor for supplying a pressurized gas to said atomizer;
    a reservoir for holding said fluid; and
    a pump for pumping said fluid from said reservoir to said atomizer.

3. The apparatus as defined in claim 1, wherein said apparatus further comprises:
    a plurality of sensors for providing signals indicative of properties of said carrier gas in said region; and
    a controller for controlling the operation of said apparatus, said controller connected to said plurality of sensors for determining a maximum rate that said fluid may be injected into said carrier gas based on signals received from said plurality of sensors.

4. The apparatus as defined in claim 3, wherein said plurality of sensors includes at least one of the following: a humidity sensor, a temperature sensor and a vaporized hydrogen peroxide concentration sensor.

5. The apparatus as defined in claim 3, wherein said plurality of sensors are disposed upstream of said inlet of said housing.

6. The apparatus as defined in claim 1, wherein a portion of said diffuser is disposed within said outlet of said housing.

7. The apparatus as defined in claim 1, wherein said heating element is disposed on an inner surface of said diffuser.

8. The apparatus as defined in claim 1, wherein said diffuser is funnel shaped.

9. The apparatus as defined in claim 8, wherein said heating element is spiral shaped.

10. The apparatus as defined in claim 1, wherein one end of said diffuser forms a curved flange portion of said diffuser.

11. The apparatus as defined in claim 1, wherein said fluid is hydrogen peroxide.

12. The apparatus as defined in claim 1, wherein said diffuser defines one side of a pathway extending between said outlet of said housing and said region.

13. The apparatus as defined in claim 12, wherein said pathway redirects said carrier gas exiting said outlet of said housing into a direction generally parallel to a floor of said enclosure.

14. The apparatus as defined in claim 12, wherein said pathway redirects said carrier gas exiting said outlet of said housing into a radially outward pattern from said outlet of said housing.

15. A method for decontaminating a region defined by an enclosure using said apparatus defined in claim 1, said method comprising the steps of:
   a. circulating a carrier gas from the region through said chamber of said housing using said blower, said carrier gas flowing through said inlet of said housing, through said chamber, through said outlet of said housing and back to said region;
   b. introducing an atomized mist of a chemical agent into said chamber using said atomizer, heating said mist using said heating element of said diffuser to form a vaporous chemical agent, wherein said vaporous chemical agent is entrained into said carrier gas to form a mixture; and
   c. conveying said mixture out of said chamber along a pathway back to said region, wherein said pathway is partially defined by said diffuser disposed relative to said outlet of said housing for redirecting said carrier gas exiting said outlet of said housing in a predetermined direction.

16. The method as defined in claim 15, wherein the rate that said atomized mist of a chemical agent is introduced into said chamber is determined based on properties of said carrier gas in said region.

17. The method as defined in claim 15, wherein said chemical agent is hydrogen peroxide.

18. The method as defined in claim 15, wherein said step c) includes redirecting said mixture in a direction generally parallel to a floor of said enclosure.

19. The method as defined in 15, wherein said step c) includes redirecting said mixture in a radially outward pattern from said chamber.

* * * * *